United States Patent
Palpu et al.

(10) Patent No.: US 7,429,397 B2
(45) Date of Patent: Sep. 30, 2008

(54) HERBAL FORMULATION AS MEMORY ENHANCER IN ALZHEIMER CONDITION

(75) Inventors: Pushpangadan Palpu, Lucknow (IN); Chandana Venkateswara Rao, Lucknow (IN); Kamal Kishore, New Delhi (IN); Yogendra Kumar Gupta, New Delhi (IN); Ramasami Kartik, Lucknow (IN); Raghavan Govindrajan, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 231 days.

(21) Appl. No.: 11/024,022

(22) Filed: Dec. 28, 2004

(65) Prior Publication Data

US 2006/0141068 A1    Jun. 29, 2006

(51) Int. Cl.
*A61K 36/906* (2006.01)
*A61K 36/28* (2006.01)
*A61K 36/00* (2006.01)

(52) U.S. Cl. .................. 424/756; 424/764; 424/725
(58) Field of Classification Search ............. 424/725, 424/756
See application file for complete search history.

(56) References Cited

U.S. PATENT DOCUMENTS

| 4,048,346 | A | * | 9/1977 | Stoller | 426/583 |
| 7,160,560 | B2 | * | 1/2007 | Pinnell | 424/725 |
| 2003/0185911 | A1 | * | 10/2003 | Qazi et al. | 424/729 |
| 2004/0116351 | A1 | * | 6/2004 | Halevie-Goldman | 514/18 |

OTHER PUBLICATIONS

DW Acc 2001-293730, Dec. 2000, DW or JP, Kumai.*
DW Acc 1997-154033, Feb. 2004, DW, Hong et al.*
DW Acc 1996-454895, Oct. 1996, DW, Cox.*

* cited by examiner

*Primary Examiner*—Christopher R Tate
*Assistant Examiner*—Randall Winston
(74) *Attorney, Agent, or Firm*—Ladas & Parry LLP

(57) ABSTRACT

The invention provides a novel herbal formulation used to improve the memory and in treatment of senile and presenile dementia as a brain tonic. Formulation(s) comprises of alcoholic extract of *Tinospora cordifolia, Centella asiatica, Withania somnifera, Mucuna pruriens* and *Curcuma longa*. The formulation can be used as an emulsion or as a soft gelatin capsule for oral dosage forms.

10 Claims, No Drawings

HERBAL FORMULATION AS MEMORY ENHANCER IN ALZHEIMER CONDITION

FIELD OF THE INVENTION

The present invention provides a novel herbal formulation useful as a brain tonic, improves the memory and helps in recalling of thoughts.

BACKGROUND AND PRIOR ART OF THE INVENTION

A major discovery of the past two decades in the field of neurosciences has been the elucidation of behavioural, neurobiological and cellular basis of learning and memory processes. The brain is an assembly of interrelated neural systems that regulates their owns and each other's activity in a dynamic, complex fashion. Morphological properties of central neurons have been very useful for the description of the functional characteristics. Learning is defined as the acquisition of information and skills, and subsequent retention of that information is called memory. Alzheimer's disease is the term used to describe a dementing disorder marked by certain brain changes, regardless of the age of onset. Accordingly, effect of a wide variety of pharmacological agents or brain lesion on cognitive behaviour have been studied and most validly interpreted as "enhancement or impairment" of learning and memory process. Learning and memory can be conceived as both psychological process as well as a change in synaptic neural connectivity. The development of scientifically validated models of ischemia induced-amnesia is vital to the analysis of the functional consequences of ischemic damage and to testing the behavioural efficacy of potentially therapeutic drugs. The role of medicinal plants in increasing the memory and acting as a brain tonic is still much underestimated. Besides this, certain oils have been found to be used as sedatives, central nervous system stimulants, adaptogens, bronchodilators, anti-stress and muscle relaxants (Singh et al, 2000). During late prenatal and early postnatal brain development, the cholinergic system in the central nervous system plays an important role in learning and memory function and that brain cholinergic hypo function causes dementia with symptoms such as memory loss and disorientation in cerebrovascular or alzheimers disease (Coyle et al 1983). Following cerebral ischemia, a reduction in the cerebral blood flow and blood oxygen occur. It has also been reported that hypoxia induces a reduction of memory and judgment that is associated with a decrease in acetylcholine synthesis (Gibson and Duffy, 1981). Principally, main characteristic of memory formation in animals, as well as in human being, is its progression from a short-lived labile form to a long-lasting stable form. During this period of consolidation, memory can be disrupted by administration of a wide variety of amnesia-inducing agents. Electro convulsive shock, hypothermia and hypoxia are non-invasive procedures that can render the animal unconscious, inducing retrograde amnesia through mechanisms correlated to the practical utility to the clinical drugs. The retrieval hypothesis postulates that amnesic agents disrupt memory recall rather than storage, as the effect of some agents diminish over time resulting in the reappearance of normal memory retention. The consolidation of information is mediated by limbic structures, with the hippocampal formation particularly playing a key role in memory processing. The major pathways have been proposed in the limbic system and cortical structures as being responsible for the neuronal interconnection of information processing. Drugs like amphetamine, caffeine-containing substances which have a stimulant activity on memory. Alzheimer's disease is not a normal part of aging—it is not something that inevitably happens in later life. Rather it is one of the dementing disorders, a group of brain diseases that lead to the loss of mental and physical functions. Alzheimer's disease is an exception, rather than rule, in old age. Alzheimer's disease or a related dementia afflicts only 5 to 6 percent of older people. Research indicates that 1 percent of the population aged 65-74 has severe dementia, increasing to 7 percent of those aged 75-84 and 25 percent of those 85 or older. The main risk factor for Alzheimer's disease is increased age. The rates of disease increase markedly with advancing age, with 25 percent of people over 85 suffering from Alzheimer's or other severe dementia. Some investigators, describing Alzheimer's may be due to heredity. The onset of Alzheimer's disease is usually very slow and gradual, seldom occurring before age 65. Over time, however, if follows a progressively more serious course. Among the symptoms that typically develop, none is unique to Alzheimer's disease at its various stages. It is therefore essential for suspicious changes to be thoroughly evaluated before they become inappropriately or negligently labeled Alzheimer's disease. Problem of memory, particularly recent or short-term memory, are common early in the course of disease. Microscopic brain tissue changes have been described in Alzheimer's disease since Alios Alzheimer first reported them in 1906. The two principal changes are senile or neuritic plaques (chemical deposits consisting of degenerating nerve cells combined with a form of protein called β amyloid) and neurofibrillary tangles (malformation within nerve cells). The plaques found in the brains of people with Alzheimer's disease appear to be made, in part, from protein molecules—amyloid precursor protein (APP)—that normally are essential components of the brain. Plaque are made when an enzyme snips APP apart at a specific place and then leaves the fragments β amyloid in the brain tissue where they come together in abnormal deposits. It has not as yet been definitely determined how neurofibrillary tangles are formed. As research on Alzheimer's disease progresses, scientists are describing other abnormal anatomical and chemical changes associated with the disease. These include nerve cell degeneration in the brain nucleus basal is of Meynert and reduced levels of the neurotransmitter acetylcholine in the brains of Alzheimer's disease victims. The clinical features of Alzheimer's disease, as opposed to the "tissue" changes, are three folds, firstly Dementia—significant loss of intellectual abilities such as memory capacity, severe enough to interfere with social or occupational functioning; secondly, Insidious onset of symptoms—subtly progressive and irreversible course with documented deterioration over time. Thirdly, Exclusion of all other specific causes of dementia by history, physical examination laboratory tests, psychometric and other studies. Research has discovered a protein, called Alzheimer's Disease Associated Protein (ADAP), in the autopsied brains of Alzheimer's patients. The proteins, which seems to appears only in people with Alzheimer's, is mainly concentrated in the cortex covering the front and side sections of the brain, regions involved in memory function. Researchers have found ADAP not only in the brain tissue but also in spinal fluid. Meanwhile, Alzheimer's disease is the most over diagnosed and misdiagnosed disorder of mental functioning in older adults. Part of the problem, already alluded to, is that many other disorders show symptoms that resemble those of Alzheimer's disease. The crucial difference, though, is that many of these disorders—unlike Alzheimer's disease—may be stopped, reversed, or cured with appropriate treatment. But they must be identified and not dismissed as Alzheimer's disease or senility. Condition that affect brain and result in intellectual, behavioural, and psychological dysfunction are referred to as "organic mental disorders". These disorders represent a broad grouping of diseases and include Alzheimer's disease. Organic mental disorders that can cause clinical problem like those of Alzheimer's disease, but which might be reversible or controlled with proper diagnosis and treatment, include the several factors such as side effects of medications; substance abuse; metabolic disorders such, thyroid problems, nutritional deficiencies, anaemia etc; circulatory disorders such as heart problem, stroke; neurological disorders such normal-pressure hydrocephalus, multiple sclerosis, etc; infections like viral or fungal of the brain; Trauma, injuries to the head; toxic factors like carbon monoxide, methyl alcohol etc and Tumours, any type within the skull-whether originating or metastasising there of. In addition to organic mental disorders resulting from these diverse causes, other forms of mental dysfunction or mental health problem can also be confused with Alzheimer's disease. These form of condition are referred to as pseudodementia. Because of many other disorders that can be confused with Alzheimer's disease, a comprehensive clinical evaluation is essential to arrive at a correct diagnosis of symptoms that looks like those of Alzheimer's disease. Such an assessment should include at least three major components firstly a through general medical workup; secondly, a neurological examination, and thirdly, a psychiatric evaluation that may include psychological or psychometric testing. Alzheimer's disease has emerged as one of the great mysteries in modem day medicine, with a growing number of clues but still no answers as to its cause. The quest to uncover its cause has the air of a veritable whodunit saga. There are some theories, which tells about the cause of Alzheimer's disease. Though none of the leading theories about the genesis of Alzheimer's disease has resolved the mystery, each has led to certain intriguing findings that suggest further investigation is needed. Two critical crossroads reached in the approach to treatment for Alzheimer's disease were firstly, the recognition of Alzheimer's disease as a disorder distinct from the normal aging process; and secondly, the realization that, in developing therapeutic and social interventions for a major illness or disability, the concept of care can be as important as cure. In the Alzheimer's disease patient, depression or delusions can aggravate dysfunction. While Alzheimer's disease remains a mystery, with its cause and cure not yet found, there's considerable excitement and hope about the new findings that are unfolding in numerous research settings. There opened a new dimension in the treatment of neurodegenerative disease with a help of traditional medicine, which has proved to be effective in studying the deadly disease in animal model. Accordingly, studies shown that the herbal formulation(s) having the property of improving the memory and used in treatment of senile and pre senile dementia as a brain tonic and acting as a central antioxidant.

OBJECT OF THE INVENTION

The main object of the present invention is to provide a novel synergistic herbal formulation used as a brain tonic, cognition and recalling of thoughts in various dosage forms viz; tablets, capsules for easy consumption.

Another objective of the present invention is to prepare herbal dosage form that improves the memory and used in treatment of senile dementia.

SUMMARY OF THE INVENTION

Accordingly, the invention provides a herbal formulation having the property of developing intellectual power as well as in quick grasping of trial been done once that is the sign of improving memory and used in treatment of dementia as a brain tonic and as a central antioxidant.

In an embodiment of the invention a synergistic herbal formulation(s) comprising the extracts of pharmacologically effective form obtained from *Tinospora cordifolia, Centella asiatica, Withania somnifera, Mucuna pruriens* and *Curcuma longa* in pharmaceutically acceptable dosage optionally along with an additive useful as brain tonic and in treatment of senile and presenile dementia.

In another embodiment of the invention the extracts/juice of the plants viz *Tinospora cordifolia, Centella asiatica, Withania somnifera, Mucuna pruriens* and *Curcuma longa* are mixed in the ratio ranging from 1:0.5:1:1:2 and 1:1:1:1:2 by weight balance by conventional additives.

In still another embodiment of the invention the extract of *Centella asiatica* is obtained from leaves.

In yet another embodiment of the invention the extract of *Tinospora cordifolia* is obtained from stem.

In another embodiment of the invention the extract of *Withania somnifera* is obtained from root.

In still another embodiment of the invention the extract of *Mucuna pruriens* is obtained from seeds In yet another embodiment of the invention the extract of *Curcuma longa* is obtained from rhizomes.

In still another embodiment of the invention the formulation contains starch, lactose, acacia as additives.

In another embodiment of the invention the formulation is used in a soft gelatin capsule of oral dosage forms.

In still another embodiment of the invention the formulation has the property of improving the intellectual power of memorising and used in treatment of senile dementia as a brain tonic and as a central antioxidant.

In yet another embodiment of the invention the formulation ameliorates the symptoms of disease and to improve the general health of the patient.

In another embodiment of the invention the formulation is used to cross the blood brain barrier and leads to enhancement in the superoxide dismutase in frontal cortex.

In another embodiment of the invention the formulation is used to cross the blood brain barrier and leads to enhancement in the catalase in frontal cortex.

In yet another embodiment of the invention the formulation is used to cross the blood brain barrier and leads to enhancement in the glutathione peroxidase in frontal cortex.

In still another embodiment of the invention the formulation is used to cross the blood brain barrier and leads to enhance the superoxide dismutase in the striatum.

In yet another embodiment of the invention the said formulation is used to cross the blood brain barrier and leads to enhance the catalase in the striatum.

In another embodiment of the invention the formulation is used to cross the blood brain barrier and leads to enhance the glutathione peroxidase in the striatum.

In yet another embodiment of the invention the formulation is used to cure migraine and anaemia.

In another embodiment of the invention the formulation shows anti-inflammatory activity and pain reduction activity.

In still another embodiment of the invention the formulation is used in the treatment of anticonvulsant activity.

In another embodiment of the invention the formulation at different dose of 100, 200 and 400 mg/kg did not showed any toxicity in rats as well as no change in organ body weight.

In still another embodiment of the invention the synergistic formulation at a dose ranging from 100-200 mg/kg on passive avoidance test showed significant activity.

The present invention also provides a method of treating Alzheimers disease, comprising the step of administering an effective amount to patient of the herbal composition, together with or in combination with therapeutically acceptable additives.

DETAILED DESCRIPTION OF THE INVENTION

The present invention provides a novel herbal formulation useful in the treatment of alzheimers. The herbal dosage form obtained from the fresh leaves extract of *Centella asiatica* is having a potential memory-enhancing role and also found to be effective in producing tranquilizing effects, stem extract of *Tinospora cordifolia*, the root extract of *Withania somnifera*, the seeds extract of *Mucuna pruriens* and the rhizomes extract of *Curcuma longa* synergistically shown the property of improving the memory and can be used in treatment of senile dementia as a brain tonic and as a central antioxidant. It produces a significant improvement in general ability and behavioural pattern. The plant used in the invention have following properties as reported.

*Centella Asiatica* Family: Umbelliferae

Botanical description: A slender herbaceous creeping; stem long, prostate coming off from the leaf-axils of a vertical rootstock, filiform, often reddish, and with long internodes, rooting at the nodes. Leaves 1.3-6.3 cm in diameter, several from the rootstock which often have much elongated petioles, and 1-3 from each nodes of the stems, orbulicar, reniform, rather broader than long, more or less cupped, entire or shallowly crenate, glabrous on both sides, and with numerous slender nerves from a deeply cordate base; petioles very variable in length 7.5-15 cm long or more, channeled, glabrous or nearly so; stipule short, adnate to the petioles forming a sheating base. Flower in fasicicled umbel consisting of 3-4 pink, sessile (rare pedicelled) flowers; peduncles pubescent or glabrous, short, pink bracts ovate, acute, concave, 2 beneath each umbel. Calyx-teeth 0. Petals minute, pink, ovate acute, fruit 4 mm. Long, longer than broad, ovoid, hard, with thickened pericarp, reticulate-rugose, often crowned by the persistent petals, the primary and secondary ridges distinct. Distributed through India, Ceylon and also in tropical and subtropical region of the world.

Medicinal uses: The plant is Acrid, bitter, digestible, laxative, cooling effect, tonic, and antipyretic, improve appetite (Unani), cures leucoderma anaemia, urinary discharge, disease of blood, use in insanity (Ayurveda). The plant has bad taste; soporific, sedatives to the nerves, acts as a cardiotonic clears the voice and the brain; cures hiccough, headache. The plant is considered as a useful alternative and tonic in diseases of skin, nerves. In some part of India, the people are in the habit of taking the powdered dried leaves with milk for improving their general intelligence. The leaves are said to be useful in syphilitic skin diseases, both externally and internally and on the Malabar Coast, the plant is one of the remedies for leprosy. It is also a popular remedy for slight dysenteric derangement of bowls to which children are subject: three or four leaves are given with cumin and sugar, and the pounded leaves are applied to navel. In konkan one or two leaves are given every morning to cure stuttering and the juice is applied (generally as a lep with Cadamba bark and black cumin) to skin eruption supposed to arise from heat of blood.

Phytochemistry: The alcoholic extract of herb an essential oil, green in colour and possing the strong odour of the herb, fatty oil, sitosterol and a resinous substance have been obtained. The fatty oil consists of the glyceride, linolic, lignoceric, palmitic and stearic acid. An alkaloid hydrocortylin has been obtained from the dried plant. Vellarine, peptic acids are present in the leaves and roots. The plants also contain ascorbic acid in a conc. of 13.8 mg %. A glycoside asiaticoside has been isolated from the plant. The major component of the triterpine mixture is centoic acid.

Pharmacology: The usual dose for the oral administration is 5-10 grains of the plant powder thrice daily. In larger doses, the drug is a simplifying narcotic, producing giddiness and some times coma. The alcoholic extract produce tranquilising effect in rats. It was found non-toxic up to a dose of 350-mg/kg i.p. The alcoholic and aqueous extracts antagonise spontaneous contraction and also caused relaxation of musculature of isolated ileum of rat. The alcoholic extract was found to have depressant effect in rat in toxic doses. The glycosidal fractions have a sedative action in rats. It decreases the tone and diminished the amplitude of contractions of isolated ileum of rabbit and albino rat. In anaesthetised dogs, it produces slight respiratory stimulation, hypotension and bradycardia. The alcoholic extract of entire plant was found to possess anti-protozoal activity against *E. histolytica*. (Wealth of India, 1992, 115-118; Kirtikar and Basu, Indian Medicinal Plant, Vol 5, 2001 p. 219).

*Withania Somnifera* Family: Solanaceae

Botanical description: An erect, evergreen, grayish tomentose shrub 0.3-2 m tall, with fairly long, stout, fleshy, whitish-brown roots. Leaves simple, alternate or subopposite, broadly ovate, glabrous, 5-12 cm long and 2.5-7 cm wide, apex subacute, base un equal, margins entire, finely stellate-pubescent beneath; main nerves about 6 pairs; petioles 0.3-1.7 cm long.

Phytochemistry: Two new withnolides- 5-dehydroxy withnolide R and with a somniferin A isolated and their structure established (Phytochemistry 1991). Isolation of two new withnolides sominone and sominolide and their characterization as 1alpha, 3beta, 27-trihydroxy 14 α, 15 α-epoxy 1-oxo-22(R) with a-2,24 dienolide respectively (Heterocycles 1992). Withasomidienone isolated and characterized as 27-hydroxy-3-ozo-22(R)- with a-1,4,24-trienolide (J. Nat. Prod 1991).

Pharmacology: The roots are considered alternative, germicidal, aphrodisiac and diuretic; they are used in Ayurveda to treat ulcers, fever, dyspnoea, cough, consumption, dropsy, rheumatism, toxicosis and memory loss. The powdered roots mixed with equal parts of honey and ghee is thought to be beneficial for impotence or seminal debility. The roots as well as the bruised leaves are also used externally to treat ulcers, painful swellings and scabies. The total alkaloids present in the roots produce relaxant and anti spasmodic effects. The fruits and seeds are diuretic. The leaves are considered anthelmintic and bitter, and their infusion is given to relieve fever.

*Tinospora Cordifolia* Family: Menispermaceae

Botanical Descriptions: A large glabrous climbing shrub. Stems rather succulent with long filiform, aerial roots arising from branches. Bark; warty, papery thin, creamy white or grey brown. Peels off easily. Wood, soft, perforated. Leaves; membranous, cordate with broad sinus. Pointed at the tip. Flowers; unisexual and greenish, in long clusters. Seeds; curved. Drupes; ovoid, succulent, lustrous, red, pea sized. Fruits; fleshy, one seeded. During the summer flowers and fruits during the winter. It is found throughout tropical India, ascending to an altitude of 300 m Medicinal Uses: Useful in bilious fever, rheumatism, general debility, seminal weakness, splenic diseases and urinary affections. Fresh plant is considered more efficacious. It is mostly used for preparing a kind of starch known as Guduchi satva or Sat giloe.

Phytochemistry: Sesquiterpene tinocordifolin, sesquiterpene glucoside tinocordifolioside, tinosponone, tinocordioside, cordioside, furanoid diterpenes, a new clerodane furanoditerpene viz. columbin, tinosporaside, an immunologically active arabinogalactan, two phytoecdyyones viz., ecdysterone and makisterone and several glycosides isolated as polyacetates. Other alkaloids viz., jatrorrhizine, palmatine, berberine, tembeterine, phenylpropene disaccharides cordifolioside A, B and C, choline, tinosporic acid, tinosporal, tinosporon, 20-β-hydroxyecdysone, palmatoside C and F, cordifolisides D and E, diterpenoid furanolactones.

Pharmacology: The water and ethanolic extract inhibited the cyclophosphamilde-induced immunosupression. Aqueous extract of the stem showed anti-inflammatory, analgesic and antipyretic properties in rats. In clinical studies, it also showed immunosuppressive effect in obstructive jaundice patients, antioxidant activity and amelioration of cylcophosphamide-induced toxicity.

*Mucuna Pruriens*

Botanical Description: Pantropical in distribution, it is found almost throughout India and in the Andaman and Nicobar Islands in damp habitats, ravines and scrub forests. Occasionally cultivated. A large, pubescent, herbaceous or sometimes woody, annual climber. Leaves trifoliate, leaf rachis 5-12 cm long, appressed silky; stipules linear, about 4 mm long; leaflets membranous, 7.5-12.5 cm long and 5-7.5 cm wide, ovate-rhomboid, asymmetrical, apex obtuse or acute, base rounded or truncate, both surfaces grey silky-pubescent. Flower purple, borne in pendant, axillary, 6-30 flowered racemes 15-30 cm long, the flowers solitary or 2-3 together along a slender silky rachis; pedicels 3-6 mm long, hairy; bracteoles 8 mm long, hairy; calyx 1 cm long, silky with a few irritant bristles, tube campanulate, upper teeth connate into a triangular lip as long as the tube, lateral teeth lanceolate and as long as the tube; corolla 2.5-3.7 cm long, keel slightly incurved. Fruit (pod) S-shaped, thick, turgid, 5-10 cm long and 1.2-1.8 cm wide, longitudinally ribbed, densely covered with yellow-brown stinging hairs; seeds 4-6, black, ovoid, 1.2 cm long. Flowers and fruits almost throughout the year but mainly between August and January in central Indian deciduous forest regions.

Medicinal uses: The plant is highly valued in traditional Indian medicine. The seeds and the hairs covering the pods are considered a powerful aphrodisiac in Ayurveda medicine; they are also used to treat impotence, leucorrhoea and urinary troubles. The roots are tonic; stimulant and diuretic. Seeds are used as an anthelmintic, nerve tonic and also in scorpion sting.

Phytochemistry: *M. pruriens* seeds have been reported to be a good source of 3,4-dihydroxyphenylalanine (L-dopa). Damodaran and Ramaswamy (1937) have reported the isolation of L-dopa from seeds in a yield of 1.5 percent. The alcoholic extract of *M. Pruriens* seeds gave four alkaloids viz., mucunine, mucunadine, Prurienine and prurieninine. The 80 percent alcoholic extract of seeds showed the presence of 5 indolic compounds, two of which were identified as tryptamine and 5-hydroxytryptamine. Different parts of *M. pruriens* except trichomes of pods yielded four indole-3-alkylamines. Choline was reported in all parts of the plant. The trichomes of pods gave only 5-hydroxytryptamine, whereas the stem-leaf showed the presence of 6-methoxyharman. *M. pruriens* seed oil was found to contain stearic, palmitic, myristic, arachidic, oleic, linoleic acid and a sterol.

Pharmacology: The claim of Ayurvedic physician that *M. pruriens* is effective in the treatment of parkinsonism, has prompted many pharmacologists and clinicians to investigate its effect on central nervous system. The powdered seed extract of *M. Pruriens* was devoid of anticholinergic activity. The extract showed hypotensive action in dogs and spasmodic action in guinea pig preparation, the effect being blocked by mepyramine maleate and not by atropine sulphate. The extract had no effect on frog rectus, but revealed a histaminergic activity. The observation suggested that the seed powder may act by some mechanism other than through anticholinergic property in parkinsonism. Various fractions obtained from *M. pruriens* seeds were evaluated against oxotremorine-induced tremors in mice and reserpine-induced rigidity, hypokinesia and catatonia in rats. The result indicated that the extract had no antocholinergic activity but had a potent antiparkinsonian effect, which was not however, entirely due to L-dopa. The L-dopa free fraction of the seed showed significant anti-parkinsonian activity at a dose of 200 mg/kg ip.

*Curcuma Longa* Family: Zingiberaceae

Botanical description: The genus *Curcuma* comprising about fifty species, distributed in tropical and subtropical regions of Asia, belongs to the tribe Hedychieae and consists of a rather homogenous group of rhizomatous perennials. Govindarajan (1980 Food Science and Nutrition, 14:119-301 and 1982 Food Science and Nutrition, 17:1-258) published critical reviews on turmeric *C. longa*. The taxonomic status of *Curcuma heyneana* was discussed by Firman et al; 1988 (*Phytochem.* 27:3887-3891) based on essential oil analysis. Tomlinson's (1969) work based on the anatomical evidence, which has much relevance in the classification of the order Zingiberales.

Medicinal uses: Ethnobotanical details of some of the species of *Curcuma* has been reviewed and it was found that *Curcuma* is useful in the treatment of liver disorders and has a promising kind of broad spectrum hepatoprotective agent which is used in Indonesia (Lin et al., *American J. Chin. Med.*, 1995 23:243-254). *Curcuma longa* were used predominantly for endoparasites, internal and external injuries and pregnancy related conditions in ethnic community of Trinidad and Tobago. *Curcuma longa* is used as dietary intake in Nepal (Eigner and Scholz, *J Ethnopharmacol* 1999, 67(1):1-6).

Phytochemistry: Essential oils are complex mixtures of odorous and steam-volatile compounds that are deposited in the subcuticular space of glandular hair, cell organelles, idioblasts, excretory cavities and canals or exceptionally in heartwoods. In other words, they are very complex, aromatic, volatile mixture containing many different compounds. The constituents of essential oils belong to numerous classes of chemical substances, such as hydrocarbons, alcohols, aldehydes, ketones, acids, esters, oxides and ether (Thappa et al, *J. Essent. Oil Res.*, 1982,11:97-103). Essential oils largely comprises of terpenoid compounds, which constitute two or more isoprene units. Based on this, terpenoids are mainly classified into four groups viz. monoterpenes (with 2 isoprene units i.e. 10 carbon atoms) sesquiterpenes (with 15 carbon atoms), diterpenes (with 4 isoprine units i.e. 20 carbon atoms) and polyterpenes (with 5 or more isoprene units). These terpenoid compounds provide aroma and pungency to plants. The essential oil forms the basic raw materials for perfume and flavour making industries. They are also used in the cosmetics and pharmaceutical industries. Many natural essential oils are used in aromatherapy to cure and prevent illness due to their therapeutic properties and also because of their fragrance, which can influence human thoughts and emotions. Many of the essential oils are reported to have antimicrobial, insect repellent and insecticidal properties.

Pharmacological use: The genus *Curcuma* is exhibits diverse pharmacological activities against cancer and tumorgensis. Anto et al, Mutation Res., 1996, 370:127-131, has reported the anticancer and antitumour properties of *Curcuma longa*. It was demonstrated that the inhibitory effect of curcumin on DNA and RNA synthesis in cultured HeLa cells. Dietary curcumin may inhibit azoxymethanol (40 M) induced colonic neoplasia in mice (Huang et al., *Cancer Lett* 1992, 64(2):117-21). The antimicrobial properties are well known and the result reported by many researchers pointed out the antibiotic activities of *Curcuma*. Banerjee and Nigam (J. Res. Ind. Med. Yoga Homoeo., 1978, 13:63-70) reported the antibacterial and antifungal activity of various species of *Curcuma*. Molluscicidal property of *C. longa* was reported. The insecticidal property of different species of *Curcuma*, Curcumin showed anti-inflammatory effect in acute, sub acute and chronic models of inflammation in mice and rat models. The oral $ED_{50}$ in mice, against carrageenin-induced acute oedema was 100.2 mg/kg compared to 78 mg/kg of cortisone. Clinically curcumin did not produce any side effect up to 1600 mg/kg/day for 4 weeks in phase-I trials in male volunteers. Phase-II clinical trials have been conducted in patients with rheumatoid arthritis and osteoarthritis. Curcumin inhibited rat liver microsomal delta 5 and delta 6 desaturases (Shimizu et al., *Lipids* 1992, 27(7):509-12). *Curcuma* contains an active principle(s) other than curcuminoid, which can modify the metabolism of lipid and lipoproteins. Several reports suggest that curcumin as well as turmeric increase bile flow. Essential oils of turmeric have also been found to increase the bile flow. However, some investigators have found it to be ulcerogenic (Prasad et al. *J. Physiol. Pharmocol,* 1976, 20, 92). The gastric secretion was found to be reduced after 3 h in conscious rabbits by aqueous and methanolic extracts of turmeric (Sakai et al. *Chem. Pharm. Bull.* 1989, 37, 215). *Curcumin* and turmeric have been shown to protect liver against a variety of toxicants in vitro as well as in vivo. They include carbon tetrachloride, aflatoxin B-1, paracetamol iron, and cyclophosphamide in mouse, rat and duckling. Evidence for the hypocholesterolemic and hypolipidemic activities of curcumin has been provided when it was fed with diet to rats for 7 weeks at the concentration of 0.15% (Rao et al. 1970 *J. Nutri.* 100, 1307). Ethanolic extract of *C. longa* has been shown to have hypoglycemic activity in normal as well as alloxan—induced diabeties in rats. They have also isolated a lipopolysaccharide from the root of *Curcumin,* which is similar to bacterial lipopolysaccharides and is immunostimulant (Inagawa et al. *Chem Pharm Bull* 1992, 40, 994). The wound healing property of turmeric was investigated long back and its local application was found to be effective (Gujral et al., *J. Ind. Med. Association* 22, 273 1958). A sum of approximately 26 compounds has been isolated from different *Curcuma* sp. having high antioxidant activity. Curcumin did not produce any toxicity either on single administration or on repeated oral administration over a period of 6 months in rat and monkey at doses up to 800 and 1800-mg/kg day, respectively. Curcumin administered orally to patients suffering from chronic anterior ureitis (CAU) at a dose of 375 mg three times a day for 12 weeks and all the patients who received curcumin alone improved (Lal et al., *Phytother Res* 13(4):318-22, 1999). Curcuminoids from *Curcuma longa* has been reported to protect rat pheochromocytoma and normal human umbilical vein endothelial cells from $\beta A(1-42)$ insult (Kim et al., Neuroscience letters, 303, 57, 2001). Traditional Chinese herbs has bee reported to improve cognitive functions and memory of Alzheimer's disease in mouse models (Sun et al., Zhongguo ZhongYao Za Zhi, 28, 751, 2003).

The novelty of the invention is in a herbal formulation having the property of developing intellectual power as well as in quick grasping of trial been done once that is the sign of improving memory and used in treatment of dementia as a brain tonic and as a central antioxidant. The synergistic herbal formulation comprises extracts of pharmacologically effective form obtained from *Tinospora cordifolia, Centella asiatica, Withania somnifera, Mucuna pruriens* and *Curcuma longa* in pharmaceutically acceptable dosage optionally along with an additive useful as brain tonic and in treatment of senile and presenile dementia.

In one embodiment of the invention the extracts/juice of the plants viz *Tinospora cordifolia, Centella asiatica, Withania somnifera, Mucuna pruriens* and *Curcuma longa* are mixed in the ratio ranging from 1:0.5:1:1:2 and 1:1:1:1:2 by weight balance by conventional additives. The extract of *Centella asiatica* is obtained from leaves. The extract of *Tinospora cordifolia* is obtained from stem. The extract of *Withania somnifera* is obtained from root. The extract of *Mucuna pruriens* is obtained from seeds and the the extract of *Curcuma longa* is obtained from rhizomes.

The said formulation contains starch, lactose, acacia as additives.

In another embodiment of the invention wherein said formulation used in a soft gelatin capsule of oral dosage forms.

The said formulation having the property of improving the intellectual power of memorising and used in treatment of senile dementia as a brain tonic and as a central antioxidant. The formulation is known to ameliorate the symptoms of disease and to improve the general health of the patient. The said formulation is used to cross the blood brain barrier and leads to enhancement in the superoxide dismutase in frontal cortex. The said formulation is used to cross the blood brain barrier and leads to enhancement in the catalase in frontal cortex. The formulation is used to cross the blood brain barrier and leads to enhancement in the glutathione peroxidase in frontal cortex. The formulation is used to cross the blood brain barrier and leads to enhance the superoxide dismutase in the striatum. The formulation is used to cross the blood brain barrier and leads to enhance the catalase in the striatum. The formulation is used to cross the blood brain barrier and leads to enhance the glutathione peroxidase in the striatuim. The formulation is used to cure migraine and anaemia. The formulation showed the anti-inflammatory activity and pain reduction activity. The formulation is used in the treatment of anticonvulsant activity.

The formulation at different dose of 100, 200 and 400 mg/kg did not showed any toxicity in rats as well as no change in organ body weight. The synergistic formulation at a dose ranging from 100-200 mg/kg on passive avoidance test showed significant activity.

The method of treating alzheimers, comprises the step of administering an effective amount to patient of the herbal composition, together with or in combination with therapeutically acceptable additives.

As a result of intensive study conducted by the inventors with the aim of achieving aforementioned objectives, new herbal formulation(s) is having the property of improving the memory and used in treatment of amnesia as a brain tonic and as a central antioxidant. The invention thus meets the need for a new process in which the optimal proportions of long chain fatty acids vitamins, amino acids, and active therapeutic marker compounds are retained in the product and underlies the efficacy of the compound as a brain tonic.

The oleaginous edible oil according to the invention can be incorporated into a variety of food products, including, without limitation, butter, margarine, ice cream and mayonnaise-chocolate products, preparation of jaggery, water based brinks such as wines and mineral waters. The inventive oil is also suitable for encapsulation in gelatin shells to form soft gels/capsules. Regardless of the particular form in which the inventive oil is prepared, the daily dosage of the oil to experimental animals fall within the ranges set forth above. Depending on the concentration of the inventive oil in the above form, the total amount of the food product per serving or encapsulated oil etc will also vary the desired therapeutic activity.

The invention is further illustrated by the following non-limiting examples.

Formulation (F1)

| | |
|---|---|
| *Tinospora cordifolia* | 2 wt. % |
| Sucrose/Lactose | 66.7 g/1.2 g |
| Alcohol | 10 wt. % |
| Water | q.s. to make 100 ml |

Formulation (F2)

| | |
|---|---|
| *Withania somnifera* | 2 wt. % |
| Sucrose/Lactose | 66.7 g/1.2 g |
| Alcohol | 10 wt. % |
| Water | q.s. to make 100 ml |

Formulation (F3)

| | |
|---|---|
| *Mucuna pruriens* | 2 wt. % |
| Sucrose/Lactose | 66.7 g/1.2 g |
| Alcohol | 10 wt. % |
| Water | q.s. to make 100 ml |

Formulation (F4)

| | |
|---|---|
| *Centella asiatica* | 2 wt. % |
| Sucrose/Lactose | 66.7 g/1.2 g |
| Alcohol | 10 wt. % |
| Water | q.s. to make 100 ml |

Formulation (F5)

| | |
|---|---|
| *Curcuma longa* | 2 wt. % |
| Sucrose/Lactose | 66.7 g/1.2 g |
| Alcohol | 10 wt. % |
| Water | q.s. to make 100 ml |

Formulation (F6)

| | |
|---|---|
| *Tinospora cordifolia* | 2 wt. % |
| *Withania somnifera* | 2 wt. % |
| Sucrose/Lactose | 66.7 g/1.2 g |
| Alcohol | 10 wt. % |
| Water | q.s. to make 100 ml |

Formulation (F7)

| | |
|---|---|
| *Tinospora cordifolia* | 2 wt. % |
| *Withania somnifera* | 2 wt. % |
| *Mucuna pruriens* | 2 wt. % |
| Sucrose/Lactose | 66.7 g/1.2 g |
| Alcohol | 10 wt. % |
| Water | q.s. to make 100 ml |

Formulation (F8)

| | |
|---|---|
| *Tinospora cordifolia* | 2 wt. % |
| *Withania somnifera* | 2 wt. % |
| *Mucuna pruriens* | 2 wt. % |
| *Centella asiatica* | 2 wt. % |
| Sucrose/Lactose | 66.7 g/1.2 g |
| Alcohol | 10 wt. % |
| Water | q.s. to make 100 ml |

Formulation (F9)

| | |
|---|---|
| *Tinospora cordifolia* | 2 wt. % |
| *Withania somnifera* | 2 wt. % |
| *Mucuna pruriens* | 2 wt. % |
| *Centella asiatica* | 2 wt. % |
| *Curcuma longa* | 4 wt. % |
| Sucrose/Lactose | 66.7 g/1.2 g |
| Alcohol | 10 wt. % |
| Water | q.s. to make 100 ml |

Formulation (F10)

| | |
|---|---|
| *Centella asiatica* | 2 wt. % |
| *Mucuna pruriens* | 2 wt. % |
| Sucrose/Lactose | 66.7 g/1.2 g |
| Alcohol | 10 wt. % |
| Water | q.s. to make 100 ml |

Formulation (F11)

| | |
|---|---|
| *Centella asiatica* | 2 wt. % |
| *Mucuna pruriens* | 2 wt. % |
| *Curcuma longa* | 2 wt. % |
| Sucrose/Lactose | 66.7 g/1.2 g |
| Alcohol | 10 wt. % |
| Water | q.s. to make 100 ml |

*Tinospora cordifolia, Centella asiatica, Withania somnifera* and *Mucuna pruriens* and *Curcuma longa* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.

Mix the plant extracts and dissolve them in 500 ml 10% alcohol, filter the solution and add specified quantity of sugar and heat the until the sugar dissolves and then cool and make up the volume with required amount of water to make 100 ml.

The formulation is useful to a brain tonic and cognition. Accordingly, the investigation deals with the oral dosage form has been described in detail giving the formula of the ingredients along with the method and mode of usage of the standardized extract (Table 2).

TABLE 1

Effect of formulations (F1-F9) on impairment of memory acquisition in step-down test in rats (n – 10)

| Treatment (mg/kg) | Memory Parameter | |
|---|---|---|
| | Latency (Sec) | No of Mistakes |
| Control | 3.78 ± 0.01 | 18.2 ± 3.2 |
| Scopolamine 0.4 mg/kg | 8.8 ± 0.03 | 64.5 ± 7.8 |
| Scopolamine + F1 100 | 7.9 ± 0.02 | 53.0 ± 2.8 |
| Scopolamine + F2 100 | 7.8 ± 0.02 | 55.0 ± 3.1 |
| Scopolamine + F3 100 | 7.5 ± 0.02 | 49.0 ± 3.1 |
| Scopolamine + F4 100 | 6.8 ± 0.02 | 42.0 ± 3.1 |
| Scopolamine + F5 100 | 6.7 ± 0.03 | 39.0 ± 3.1 |
| F6 100 | 6.5 ± 0.02 | 42.0 ± 3.1 |
| F7 100 | 6.3 ± 0.02 | 37.7 ± 3.4 |
| F8 100 | 4.6 ± 0.02[a] | 29.7 ± 3.4[a] |
| F9 100 | 3.98 ± 0.01[c] | 21.2 ± 2.4[c] |
| Tacrine | 3.87 ± 0.02[b] | 20.6 ± 2.1[b] |

Values are mean ± S.E.M.
P: [a]<0.05 [b]<0.01 and [c]<0.001 compared to Scopolamine group.
Note:
There is no mortality/gross abnormality was observed in the animals during the treatment of Formulations (F1-F9)

The results of the Table 1 represent a significant decrease in the number of mistakes done by the animals. Whereas the scopolamine treated group showed a significant increase in the number of mistakes as well as increase the latency period.

Tacrine (1,2,3,4-tetrahydro-5-aminoacridine or THA) (Summers et al, Clinical Tox 1980; 16(3):269-281) is more effective in improving memory in Alzheimer's patients and used to treat the symptoms of Alzheimer's disease. Disadvantages of tacrine upset the stomach, vomiting, diarrhea, heartburn, muscle aches, headache, loss of appetite etc.

The formulation F1 contains the *Tinospora cordifolia* only
The formulation F2 contains the *Withania somnifera* only
The formulation F3 contains the *Mucuna pruriens* only
The formulation F4 contains the *Centella asiatica* only
The formulation F5 contains the *Curcuma longa* only
The formulation F6 contains the *Tinospora cordifolia* and *Withania somnifera* only
The formulation F7 contains the *Tinospora cordifolia*, *Withania somnifera* and *Mucuna pruriens* only
The formulation F8 contains the *Tinospora cordifolia*, *Withania somnifera*, *Mucuna pruriens* and *Centella asiatica* only
The formulation F9 contains the *Tinospora cordifolia*, *Withania somnifera*, *Mucuna pruriens*, *Centella asiatica* and *Curcuma longa* only.

Behavioral Tests

Passive avoidance task (step-down test): A step-down passive avoidance was examined using apparatus consisted of a box (25×25×40 cm), a floor with stainless-steel grid 2 mm in diameter at 8-mm intervals, and a rubber platform (4 cm diameter, 4 cm height) set on the grid in one corner. Electric stimulation was given through the grid connected with a scrambled shock generator. After 24 hr of cerebral ischemia/scopolamine (0.4 mg/kg, i.p.), an acquisition trail was performed. For this trial, each rat was placed gently on the platform and allowed to habituate freely for 3 min, and then electric shock (0.4 mA) were delivered to the grid. If the rat stepped down from the platform, the electric shock was delivered to the rat on the grid floor. The cut off time was 2 min. A retention trail was performed 24 hr after the acquisition trail. Each rat was again placed on the platform. Time (step-down latency) that elapsed until rats stepped down from the electric grid of the platform to shock free zone was recorded. If the rat did not step down from the platform within 2 min's, the retention trail was terminated and the maximal step down latency of 2 min was recorded. An error was counted when ever the rat stepped down from platform. The number of error made in 2 min was recorded.

TABLE 2

Effect of different formulation on transfer latency in i.c.v. Streptozotocin (STZ)-treated rats (n – 10).

| Treatment | Transfer latency (Sec) | | |
|---|---|---|---|
| | ITL (day 13) | 1st RTL (day 14) | 2nd RTL (day 21) |
| i.c.v. ACSF | 51.8 ± 8.2 | 22.1 ± 1.6 | 18.9 ± 3.1 |
| STZ + vehicle | 49.2 ± 4.8 | 45.2 ± 4.8 | 52.5 ± 8.1 |
| STZ + F6 100 | 48.4 ± 5.2 | 41.9 ± 5.1 | 38.9 ± 4.5 |
| STZ + F7 100 | 43.4 ± 5.2 | 39.9 ± 5.6 | 34.9 ± 4.5 |
| STZ + F8 100 | 37.4 ± 5.2 | 32.9 ± 5.8 | 27.9 ± 4.4[a] |
| STZ + F9 100 | 31.2 ± 4.2[b] | 29.8 ± 4.8[b] | 25.6 ± 4.2[b] |

Values are mean ± S.E.M.
[a]P < 0.01, [b]P < 0.001 compared with i.c.v. STZ- treated rats.
ITL, initial transfer latency after 13 days of i.c.v. STZ administration.
1st RTL, 1st retention transfer latency 24 hr after ITL.
2nd RTL, 2nd retention transfer latency 8 days after ITL.
i.c.v. ACSF (Intracerebroventricular, Artificial cerebrospinal fluid); STZ + vehicle; STZ + F6 100 mg/kg; STZ + F7 100 mg/kg; STZ + F8 100 mg/kg, STZ + F9 100 mg/kg ITL—the time taken for the rats to move from the open arm and enter into one of the closed arm was recorded as initial transfer latency (ITL).

Then, 24 hr after ITL, the rat was placed similarly on the open arm and the retention latency was noted again and the termed as 'first retention transfer latency' (1st RTL).

Then 8 days after ITL, the rat was placed similarly on the open arm and the retention latency was noted again and the termed as 'second retention transfer latency' (2nd RTL).

The formulation F6 contains the *Tinospora cordifolia* and *Withania somnifera*

The formulation F7 contains the *Tinospora cordifolia*, *Withania somnifera* and *Mucuna pruriens*

The formulation F8 contains the *Tinospora cordifolia*, *Withania somnifera*, *Mucuna pruriens* and *Centella asiatica*

The formulation F9 contains the *Tinospora cordifolia*, *Withania somnifera*, *Mucuna pruriens*, *Centella asiatica* and *Curcuma longa*.

Intracerebroventricular Administration of Streptozotocin

Immediately prior to surgery, rats were anaesthetized with chloral hydrate (240 mg/kg, i.p., in 4% solution) and positioned in a stereotaxic apparatus. A saggital incision was made in the scalp and two holes were drilled through the skull for placement of the injection cannula into the lateral cerebral ventricles. Animals received either i.c.v. artificial cerebrospinal fluid (ACSF; 10 μL/site) or i.c.v. STZ (3 mg/kg bilaterally using a microsyringe). The composition of the ACSF was (in mmol/L): Nacl 147; Kcl 2.9; Mgcl$_2$ 1.6; Cacl$_2$ 1.7; dextrose 2.2. To ensure diffusion of the administered drug, the cannula was left in place for a period of 2 min following the injection. The stereotaxic coordinates for i.c.v. injection was 0.8 mm posterior to bregma, 1.8 mm lateral to the saggital suture and 3.6 mm beneath the cortical surface.

Elevated Plus-Maze (Behavioural Test)

The plus-maze is the simple, fast and less time consuming process. There is no need of prior training or noxious stimuli (sound or light) is required It is predictable and reliable procedure for studying cognition in Alzheimer's condition and to study the effect of drug response to senile dementia. Exposure of animals to novel maze alley evokes an approach-avoidance conflict, which is stronger in open arm as compared to enclosed arm. Rodents have aversion for high and open space and preferred enclosed arm and therefore spend greater time in enclosed arm. The plus maze consists of two opposite open arms (50×10 cm), crossed with two closed arms of the same dimensions with 40 cm high walls. The arms are connected by a central square (10×10 cm). On day 13 after i.c.v STZ injection, rats were placed individually at one end of an open arm, facing away from the central square. The time taken for rat to move from open arm and enter into one of the closed arms was recorded as 'initial transfer latency' (ITL). The animal was allowed to explore the maze for 30 s after recording the ITL, the rat was placed similarly on the open arm and the retention latency was noted again and termed as 'first retention transfer latency' ($1^{st}$ RTL) and 'second retention transfer latency' ($2^{nd}$ RTL).

The formulation F8 contains the *Tinospora cordifolia*, *Withania somnifera*, *Mucuna pruriens* and *Centella asiatica* only The formulation F9 contains the *Tinospora cordifolia*, *Withania somnifera*, *Mucuna pruriens*, *Centella asiatica* and *Curcuma longa* only.

Biochemical Test

Streptozotocin Induced Oxidative Stress

The rats were killed on day 21 for estimation of oxidative stress parameter (malondialdehyde(MDA), gluthathione, superoxide dismutase, and catalase in the whole brain upon completion of the behavioral task. Following behavioral testing, animals were decapitated under ether anaesthesia and their brains quickly removed, cleaned with ice-cold saline and stored at −80° C.

Tissue preparation: Brain tissue samples were thawed and homogenized with 10 times (w/v) ice-cold 0.1 mol/l phosphate buffer (ph 7.4). Aliquots of homogenates from rat brain were separated and used to determine protein, lipid peroxidation and gluthathione. The remaining homogenates were centrifuged at 28 900 g for 60 min and the supernatant was then used for enzyme assays. Catalase activity was determined immediately after sample preparation and SOD was determined within 24 h. Protein concentration was determined according to the method of Lowry using purified bovine serum albumin as a standard.

TABLE 3

Effect of different formulation on oxidative stress markers in i.c.v. Streptozotocin (STZ)-treated rats on day 21.

| Treatment | Malondialdehyde (nmol/g tissue) | Glutathione (μg/g tissue) | Superoxide dismutase (U/mg protein) | Catalase (U/mg protein) |
| --- | --- | --- | --- | --- |
| i.c.v. ACSF | 251.6 ± 53.1 | 164.6 ± 7.4 | 3.4 ± 0.2 | 5.6 ± 2.0 |
| STZ | 436.4 ± 53.2 | 34.2 ± 1.4 | 3.6 ± 0.4 | 6.8 ± 2.1 |
| STZ + F6 (100 mg/kg) | 420.7 ± 64.6 | 42.4 ± 2.8 | 3.3 ± 0.2 | 11.6 ± 2.9 |
| STZ + F7 (100 mg/kg) | 220.4 ± 36.4 | 94.5 ± 7.8 | 3.4 ± 0.2 | 9.4 ± 1.5 |
| STZ + F8 (100 mg/kg) | 182.4 ± 26.6 | 99.6 ± 4.2 | 2.8 ± 0.4 | 17.7 ± 3.6 |
| STZ + F9 (100 mg/kg) | 174.9 ± 24.8[a] | 108.4 ± 4.1[a] | 2.5 ± 0.2 | 14.2 ± 2.8[a] |

Values are the mean ± SEM.
[a]$P < 0.001$ compared with i.c.v. streptozotocin (STZ) vehicle-treated rats. F9 shows the highest antioxidant activity compared with other formulations with respect to STZ treated rats.

The results of Table 3 represent a significant antioxidant activity by decreasing the level of malondialdehyde in the brain of i.c.v. STZ rats treated with F6, F7, F8 and F9 formulation at a dose of 100 mg/kg compared with the vehicle-treated i.c.v. STZ rats indicate attenuation of lipid peroxidation. There is simultaneously significant decrease in reduced gluthathione levels in vehicle-treated i.c.v. STZ rats. The increase in the gluthathione level in F9 treated i.c.v. STZ groups are due the antioxidant property.

The formulation F6 contains the *Tinospora cordifolia* and *Withania somnifera* only The formulation F7 contains the *Tinospora cordifolia*, *Withania somnifera* and *Mucuna pruriens* only

TABLE 4

Effect of formulation (F9) in frontal cortex region in rat brain and the levels of superoxide dismutase (SOD), catalase (CAT), and glutathione peroxide (GPX).

| S. No | Treatment (100 mg/kg) | GPX (U/mg protein) | CAT (U/mg protein) | SOD (U/mg protein) |
| --- | --- | --- | --- | --- |
| I | Normal | 0.052 ± 0.01 | 13.9 ± 2.4 | 14.2 ± 1.4 |
| II | F9 | 0.16 ± 0.007[c] | 28.8 ± 0.9[c] | 24.6 ± 2.5[c] |

Values are mean ± SEM.
P: [c]$<0.001$, compared to control group.

The F9 formulation contains *Tinospora cordifolia*, *Withania somnifera*, *Mucuna Pruriens*, *Centella asiatica* and *Curcuma longa* only.

From the table the F9 formulation shows the effective significant GPX, CAT and SOD compared with the normal. This is because of the presence of *Curcuma longa* present in the F9 formulation.

TABLE 5

Effect of formulation (F9) on rat brain in stratium of brain region and the levels of superoxide dismutase (SOD), catalase (CAT), and glutathione peroxidase (GPX).

| S.No | Treatment (100 mg/kg) | GPX (U/mg protein) | CAT (U/mg protein) | SOD (U/mg protein) |
|---|---|---|---|---|
| I | Normal | 0.076 ± 0.008 | 18.7 ± 2.2 | 15.3 ± 2.4 |
| II | F9 | 0.19 ± 0.012$^c$ | 38.6 ± 1.3$^c$ | 30.5 ± 1.3$^c$ |

Values are mean ± SEM.
P: $^c$<0.001, compared to control group.

The F9 formulation contains *Tinospora cordifolia*, *Withania somnifera*, *Mucuna Pruriens*, *Centella asiatica* and *Curcuma longa* only.

From the table the F9 formulation shows the effective significant GPX, CAT and SOD compared with the normal. This is because of the presence of *Curcuma longa* present in the F9 formulation.

TABLE 6

Effect of Formulations (F6-F9) on λ carrageenin induced edema in rats.

| Treatment (mg/kg) | Dose (mg/kg) | Paw volume (ml) at 3 h | |
|---|---|---|---|
| | | λ carrageenin | % Inhibition |
| Control | — | 0.87 ± 0.02 | — |
| Formulation F6 | (100 mg/kg) | 0.78 ± 0.02 | 10.34 |
| Formulation F7 | (100 mg/kg) | 0.68 ± 0.04 | 21.83 |
| Formulation F8 | (100 mg/kg) | 0.57 ± 0.04 | 34.48 |
| Formulation F9 | (100 mg/kg) | 0.19 ± 0.04$^c$ | 78.16 |
| Formulation F10 | (100 mg/kg) | 0.63 ± 0.04 | 27.58 |
| Formulation F11 | (100 mg/kg) | 0.56 ± 0.04 | 35.63 |
| Indomethacin | (100 mg/kg) | 0.18 ± 0.02$^c$ | 79.31 |

Values are mean ± SEM for six rats.
P: $^c$<0.001 compared to control group.

The formulation F6 contains the *Tinospora cordifolia* and *Withania somnifera* only The formulation F7 contains the *Tinospora cordifolia*, *Withania somnifera* and *Mucuna pruriens* only The formulation F8 contains the *Tinospora cordifolia*, *Withania somnifera*, *Mucuna pruriens* and *Centella asiatica* only The formulation F9 contains the *Tinospora cordifolia*, *Withania somnifera*, *Mucuna pruriens*, *Centella asiatica* and *Curcuma longa* only.

The formulation F10 contains the *Centella asiatica* and *Mucuna pruriens*

The formulation F11 contains the *Centella asiatica*, *Mucuna pruriens* and *Curcuma longa* only.

From the table the F9 formulation shows the effective significant anti-inflammatory action against control compared with the other formulations. This is because of the presence of *Curcuma longa* present in the F9 formulation. Indomethacin is a synthetic bioactive molecule used in treatment of inflammation only. The disadvantage of the molecule indomethacin is it causes gastric ulcer.

Antiinflammatory Activity

Carrageenin induced paw edema: Rats were injected with 0.1 ml of 1% λ carrageenin (St.-Louis, Mo.) into the subplantar side of the left hind paw. The paw was marked with ink at the level of the lateral malleolus and dipped in perspex cell up to this mark. The paw volume was measured with an Ugo Basile Plethysmometer (No: 61402) (7140 Comerio-varese, Italy) immediately and 3 h after injecting the λ carrageenin suspension. The Formulation (F9) was administered at dose of 100 mg/kg respectively orally by gavage 1 h before the λ carrageenin injection. Significant reductions in the paw volume compared to vehicle treated control animals were considered as anti-inflammatory response. Percentage inhibition of oedema was calculated as follows:

% Inhibition=$(1-V_T/V_C) \times 100$ $V_T$=Paw volume in drug treated rats, $V_C$=Paw volume in control group of rats.

TABLE 7

Effect of formulation (F9) on relative mean ± SEM organ weights of rats (n = 6)

| Type of treatment | Treatment group (mg/kg) | Body weight (g) | Kidney (g) | Liver (g) | Spleen (g) |
|---|---|---|---|---|---|
| | Control | 149.8 ± 10.2 | 1.02 ± 0.04 | 5.78 ± 0.42 | 0.68 ± 0.05 |
| 6 days | F9 100 | 152.2 ± 11.4 | 0.99 ± 0.02 | 5.82 ± 0.51 | 0.71 ± 0.02 |
| oral | F9 200 | 150.5 ± 10.8 | 0.92 ± 0.06 | 5.94 ± 0.44 | 0.70 ± 0.8 |
| treatment | F9 400 | 156.4 ± 11.4 | 0.98 ± 0.04 | 5.81 ± 0.64 | 0.62 ± 0.04 |

Values are mean ± S.E.M.

F9 formulation contains mixture of *Tinospora cordifolia, Withania somnifera, Mucuna pruriens, Centella asiatica* and *Curcuma longa* only The results of the Table 7 shows there is no significant changes in body weight of various vital organs in the body in toxicity studies at a higher dose of 400 mg·kg.

Therefore the formulation F9 is highly effective and it is safe (Table 1).

Note: No mortality/gross abnormality was observed in the animals during the treatment of F9 containing formulation.

We claim:

1. A composition useful for the treatment of senile or presenile dementia comprising extracts obtained from *Tinospora cordifolia, Centella asiatica, Withhania somnifera, Mucuna pruriens* and *Curcuma longa,* wherein the composition comprises said extracts in a ratio ranging from 1:0.5-1:1:1:2, respectively, and one or more physiologically acceptable additives.

2. The composition as claimed in claim 1 wherein the extract of *Centella asciatica* is obtained from leaves of *Centella asciatica.*

3. The composition as as claimed in claim 1 wherein the extract of *Tinospora cordifolia* is obtained from stems of *Tinospora cordifolia.*

4. The composition as as claimed in claim 1 wherein the extract of *Withania somnifera* is obtained from roots of *Withania somnifera.*

5. The composition as claimed in claim 1 wherein the extract of *Mucuna pruriens* is obtained from seeds of *Mucuna pruriens.*

6. The composition as claimed in claim 1 wherein the extract of *Curcuma longa* is obtained from rhizomes of *Curcuma longa.*

7. The composition as claimed in claim 1 wherein said additives are starch, lactose, and acacia.

8. The composition as as claimed in claim 1 wherein said composition is in the form of a soft gelatin capsule.

9. A method of treating Alzheimer's, comprising the step of administering an effective amount to patient of the composition as claimed in claim 1, together with or in combination with therapeutically acceptable additives.

10. Method as claimed in claim 9 wherein the formulation is used at a dose ranging from 100-200 mg/kg.

* * * * *